United States Patent [19]

Shuto et al.

[11] Patent Number: 5,187,174
[45] Date of Patent: Feb. 16, 1993

[54] 6'-DEOXY-6'-HALO-NEPLANOCIN A AND ITS PRODUCTION

[75] Inventors: Satoshi Shuto; Takumi Obara; Hiromichi Itoh; Takehiro Koshio; Tatsuro Fujiwara; Masao Yaso, all of Shizuoka, Japan

[73] Assignee: Asahi Kasei Kogyo Kabushiki Kaisha, Osaka, Japan

[21] Appl. No.: 673,177

[22] Filed: Mar. 18, 1991

Related U.S. Application Data

[63] Continuation of Ser. No. 477,520, Feb. 9, 1990, abandoned.

[30] Foreign Application Priority Data

Feb. 14, 1989 [JP] Japan .................................. 1-34748

[51] Int. Cl.$^5$ ..................... A61K 31/52; C07D 473/00
[52] U.S. Cl. .................... 514/261; 544/277
[58] Field of Search .................... 544/277; 514/261

[56] References Cited

U.S. PATENT DOCUMENTS 4,613,666 9/1986 Fukukawa et al. .................. 544/277
4,816,575 3/1989 Fukukawa et al. .................. 544/277

FOREIGN PATENT DOCUMENTS 835405 4/1982 Japan .
58-118586 7/1983 Japan .
58-183691 10/1983 Japan .
59-219284 12/1984 Japan .

OTHER PUBLICATIONS

R. Vince et al. Bioc. Biop. Res. Com. vol. 156(2) 1046-1053 (1988).
Fessenden & Fessenden "Organic Chemistry, 2nd ed." (1982) pp. 262-272.
"Neplanocins, New Antitumor Agents: Biological Activites", *Proceedings of the 11th ICC and the 19th ICAAC,* 1980, By M. Tsujino et al., pp. 1559-1561.
"Biochemical Mode of Cytotoxic Action of Neplanocin A in L1210 Leukemic Cells", *Cancer Research,* vol. 46, Mar. 1986, By M. Inaba et al., pp. 1063-1067.

*Primary Examiner*—Mukund J. Shah
*Assistant Examiner*—Matthew Grumbling
*Attorney, Agent, or Firm*—Young & Thompson

[57] ABSTRACT

A compound of the formula

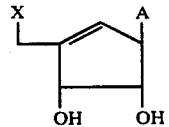

wherein A is adenine-9-yl and X is halogen, Preferably iodine, or a pharmaceutically acceptable salt thereof. It is a novel derivative of neplanocin A and has almost the same level of cytotoxic activity. However, it is not inactivated by the action of adenosine deaminase. It is produced by replacing a hydroxyl at position-6' in neplanocin A or 2', 3'-O-protected neplanocin A with halogen by use of a halogenating agent, and when hydroxyl at position-2' or -3' is protected, removing the protective group thereof.

2 Claims, No Drawings

6'-DEOXY-6'-HALO-NEPLANOCIN A AND ITS PRODUCTION

This application is a continuation of application Ser. No. 477,520, filed Feb. 9, 1990, abandoned.

FIELD OF THE INVENTION

This invention relates to a novel neplanocin A derivative having antiproliferative activity and to pharmacologically acceptable salts thereof.

PRIOR ART

Neplanocin A is a compound represented by the formula

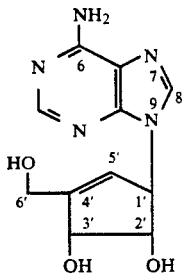

which has cytotoxic activity in vitro [Proceedings of 11th International Congress of Chemotherapy, Vol. 2, 1559–1561 (1979)] (hereinafter designated as Ref. 1). However its cytotoxic activity is not sufficient for use as an anti-proliferative agent. Derivatives of neplanocin A have also been synthesized [Japanese Patent Unexam. Publ. No. 57-163383, ibid. No. 57-102889, ibid. No. 58-85898, ibid. No. 58-118586, ibid. No. 58-183691, ibid. No. 59-219284]; however, no derivatives superior to neplanocin A have been discovered.

PROBLEMS TO BE SOLVED BY THE PRESENT INVENTION

The cytotoxic activity of neplanocin A was discovered after phosphorylation of hydroxyl at position-6 thereof by the action of kinase in the cells [Cancer Res., 46:1063-1067 (1986)] (hereinafter designated as Ref. 2). It is therefore thought to have no action on the cells having no kinase activity for neplanocin A as a substrate. Also the cytotoxic activity of neplanocin A in vivo is thought to be reduced by the action of adenosine deaminase, which is widely distributed in vivo, with rapid conversion to an inert deamination-type compound (neplanocin D) (Ref. 1).

Therefore novel derivatives of neplanocin A which are not inactivated by the action of adenosine deaminase, would be highly desirable.

MEANS FOR SOLVING THE PROBLEMS

We have found that a novel 6'-deoxy-6'-haloneplanocin A of the formula [1] is not inactivated by adenosine deaminase and has almost the same level of cytotoxic activity as known neplanocin A. Moreover a compound [1] of the present invention has no hydroxyl group at position-6' to be affected by enzymatic phosphorylation; however, quite surprisingly, it has an equal level of cytotoxicity as does neplanocin A, and hence the present compound is useful as an antiproliferative agent.

An object of the present invention is to provide a novel compound of the formula

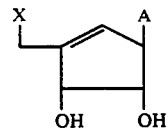

wherein A is adenine-9-yl and X is halogen, or a pharmacologically acceptable salt thereof.

Another object of the present invention is to provide a process for the production of compound [1] above or a pharmacologically acceptable salt thereof.

Such a pharmacologically acceptable salt is a non-toxic salt. Examples thereof are inorganic salts such as hydrochloride, sulfate or phosphate and organic salts such as acetate, propionate, tartrate, citrate, glycolate, gluconate, succinate, malate, glutamate, aspartate or methanesulfonate. Other non-toxic salts with organic acids are included.

A compound [1] of the present invention can be obtained by replacing the hydroxyl at position-6' in neplanocin A or 2',3'-0-protected neplanocin A with halogen by use of a halogenating agent, and when hydroxyl at position-2' or -3' is protected, removing the protective group or groups thereof, and if required preparing a pharmacologically acceptable salt thereof.

According to another method, a process for production of the compound [1c] of the formula

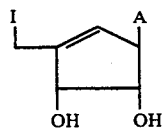

wherein A is adenine-9-yl, or pharmacologically acceptable salt thereof, comprises replacing the halogen at position-6' in a compound of the formula

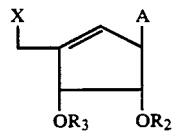

wherein A is adenine-9-yl, X is chlorine or bromine, and $R_2$ and $R_3$ are hydrogen or a protective group for hydroxyl, with iodine by use of an iodinating agent, and when hydroxyl at position-2' or -3' is protected, removing the protective group or groups thereof, and if required preparing a pharmacologically acceptable salt thereof.

The above 2', 3'-0-protected neplanocin A is a compound wherein the hydroxyl groups at positions 2' and 3' in neplanocin A are protected by a known protective group used in nucleic acid chemistry. Examples of such protective groups are a ketone compound residue in which cyclic acetal is formed together with two adjacent oxygen atoms, for example isopropylidene, methoxymethylene, methoxyethylidene, ethoxymethylene, benzylidene and cycloalkylidene. These protective groups can be introduced by reaction with a corresponding aldehyde or ketone compound in the presence of an acid catalyst. Furthermore, hydroxyl at position-2' and -3' can also be protected by acyl groups such as formyl, acetyl, chloroacetyl, trichloroacetyl, trifluoroacetyl, methoxyacetyl, pyvaloyl, benzoyl, β-benzoylpropionyl or trityloxyacetyl, a trityl group such as trityl, monomethoxytrityl, dimethoxytrityl or trimethoxytrityl, or methoxymethyl.

In the present invention, a compound [1] can preferably be produced by the following process according to the identity of X in compound [1].

(A) A process for production of a compound [1a] wherein

X is Cl or Br":

A compound [1a] can be produced by halogenating neplanocin A with a halogenating agent using triphenylphosphine and $CCl_4$ or $CBr_4$ as solvent.

An example of a reaction solvent hereinabove is an organic solvent such as dimethylformamide or hexamethylphosphoric triamide. The halogenation reaction can proceed, in general, at room temperature. The process of the reaction can be traced by silica gel thin layer chromatography (TLC) or high performance liquid chromatography (HPLC), so that the reaction can be terminated when maximum production of compound [1a] is observed.

Isolation of the compound [1a] can be performed by stopping the reaction by adding an alcohol such as methanol, removing the solvent, adding a solvent such as chloroform, and filtering the thus-formed insoluble product [1a].

Another method of halogenation uses a halogenating agent such as $SOCl_2$ or $SOBr_2$. A compound [1a] wherein X is Cl, can preferably be produced by using $SOCl_2$.

The thus-produced compound [1a] can be purified by column chromatography using silica gel or an adsorption resin with an elution solvent such as chloroform-methanol.

(B) A process for production of a compound [1b] wherein

X is F:

A compound [1b] can be produced by fluorinating 2',3'-o-protected neplanocin A [2] with a fluorinating agent using diethylamino sulfatrifluoride as a reaction solvent, and removing the protective groups for hydroxyl at position-2' and -3'.

Examples of the above reaction solvents are organic solvents such as dichloromethane, chloroform or dichloroethane. The fluorination reaction can proceed under ice cooling. The progress of the reaction can be traced by TLC or HPLC, so that the reaction can be terminated when maximum production of a compound [1b] is observed.

Isolation of the thus-obtained 6'-deoxy-6'-fluoro-2',3'-O-protected neplanocin A [3] can be performed by adding an aqueous alkali such as sodium bicarbonate solution to stop the reaction, adding an extraction solvent such as chloroform, filtering out the insoluble material, separating the filtrate, and concentrating the organic layer. Further purification can be effected by column chromatography using silica gel or an adsorption resin with an elution solvent such as chloroform-methanol.

A compound [1b] can be obtained by removing the protective groups for hydroxyl at positions 2' and 3' in production [3] by means of known removal techniques used in nucleic acid chemistry. For example, isopropylidene can be removed by treating with an aqueous acid such as aqueous formic acid or acetic acid.

Isolation of the thus-obtained compound [1b] can be performed by removing the aqueous acid, treating the residue with an organic solvent such as tetrahydrofurance for crystallization, or by means of column chromatography using silica gel or adsorption resin with an elution solvent such as chloroform-methanol.

(C) Process for production of a compound [1c] wherein X is I:

A compound [1c] can be produced by iodinating the halogen at position-6' in the compound [1a] with an iodinating agent, e.g. an alkali metal iodide, in a reaction solvent.

An example of a reaction solvent is an organic solvent such as acetonitrile. Examples of alkali metal iodides are LiI and NaI. The iodination reaction can be performed with refluxing of the reaction solvent.

Isolation and purification of the compound [1c] can be effected by removing the reaction solvent, dissolving the residue in methanol, and subjecting this solution to column chromatography using silica gel or an adsorption resin elution solvent such as chloroform-methanol.

A pharmacologically acceptable salt of the thus-obtained compound [1] can be prepared, if desired, by any known method.

EFFECT OF THE INVENTION

The growth inhibition activity of L5178Y cells and the resistance to adenosine deaminase of a compound [1] of the present invention are illustrated hereinbelow.

1. Growth inhibition activity against L5178Y cells:

A solution of each test compound is prepared by dissolving or suspending the compound in RRMI 1640 medium containing 10% bovine serum by ultrasonication. A cell suspension of L5178Y cells, $1.1 \times 10^4$ cells/ml, each suspension having a volume of 1.8 ml, is added to each test tube. A solution (0.2 ml) of the test compound hereinabove is added thereto and the medium is tightly sealed and incubated at 37° C. for 48 hours. After incubation, the number of cells is measured using a Coulter counter and the growth ratio of the cells is determined.

The results are shown in Table 1.

TABLE 1

| Growth Inhibition of L5178Y Cells | | |
| --- | --- | --- |
| Test Sample | | $IC_{50}$ (µg/ml) |
| Control | Neplanocin A | 0.2 |
| Compound (1) | X = Cl | 0.3 |
| | X = Br | 0.2 |
| | X = F | 1.1 |
| | X = I | 0.4 |

2. Resistance to adenosine deaminase:

A solution 0.5 mM of each test sample is prepared by dissolving the test sample in 0.05M Tris-HCl buffer (pH 7.2). Adenosine deaminase (calf intestine, 400 U/ml glycerin, Boehringer 102091) is diluted ten times with 0.05M Tris-HCl buffer (pH 7.2) to prepare an adenosine deaminase solution.

0.5 ml of each sample solution is mixed with 10 µl of adenosine deaminase solution. The mixtures are allowed to stand in a water bath at 25° C., and 4 µl samples thereof are pipetted off after 1, 10, 20 and 30 minutes. The remaining sample is measured by HPLC under the following conditions:

| HPLC: | |
| --- | --- |
| Column: | Licrosorb RP-18-5 |
| Elution solvent: | Control; 15% methanol |
| Compound: | 25% methanol |
| Elution speed: | 1.0 ml/min. |
| Temperature: | 50° C. |

-continued

| Detection: | 260 nm UV |
|---|---|
| Injection volume: | 4 μl |
| Retention time: | |
| Control: | 2.2 min. |
| Compound (1); X = Cl: | 3.9 min. |
| X = Br: | 4.5 min. |
| X = F: | 2.4 min. |
| X = I: | 6.5 min. |

The results are shown in Table 2.

TABLE 2

| Test Sample | | Remaining Amount (%) | | |
|---|---|---|---|---|
| | | 10 min. | 20 min. | 30 min. |
| Control | Neplanocin A | 6 | 0.4 | 0 |
| Compound (1) | X = Cl | 101 | 99 | 102 |
| | X = Br | 98 | 97 | 97 |
| | X = F | 99 | 98 | 98 |
| | X = I | 97 | 96 | 96 |

As shown by the above, the compounds (1) of the present invention have growth inhibitory activity against L5178Y cells at almost same levels as known neplanocin A. However, these compounds (1) are not decomposed by adenosine deaminase even after 30 mins. of incubation and hence they have very high resistance which is much greater than that of known neplanocin A. The cytotoxic action of neplanocin A is said to be manifested by enzymatic phosphorylation of hydroxyl at position-6'. In spite of having no hydroxyl group at position-6', which is to be phosphorylated, in the compounds (1) of the present invention, it is quite unexpected to have cytotoxic activity and hence the new compounds are useful as antiproliferative agents.

The following examples illustrate the present invention but are not to be construed as limiting:

EXAMPLE 1

Production of 6'-deoxy-6'-chloroneplanocin A:
Hexamethyl phosphoric triamide (HMPA) (1 ml) and thionyl chloride (150 μl) were added to neplanocin A (80 mg) (0.3 m mol), and the mixture was stirred at room temperature for two hours. The reaction mixture was charged on a column (2×5 cm) of silica gel (Wako Pure Chem. Co., C-200) and eluted with chloroform, chloroform-methanol (20:1) and chloroform-methanol (5:1) in this order. The fraction eluted with chloroform-methanol (5:1) was concentrated in vacuo. Isopropanol was added to the residue, which was concentrated twice in vacuo and the residue was kept under refrigeration overnight. The product, dissolved in a small amount of methanol, was neutralized with 0.5N sodium bicarbonate solution and the solvent was removed. The residue was purified by preparative chromatography using a silica gel plate (Merck, Art 5717) (developer: chloroform-methanol (6:1), elution: chloroform-methanol (2:1)) and recrystallized from ethanol to obtain the compound (52 mg).

Elementary analysis ($C_{11}H_{12}N_5O_2Cl \cdot \frac{1}{2} H_2O$):
Theoretical: C: 45.45, H: 4.85, N: 23.37, Cl: 11.83;
Found: C: 45.03, H: 4.54, N: 23.31, Cl: 11.87.
UV; λ max 260 nm (water).
$^1$H-NMR (400 MHz, $CD_3 OD$) δ; 4.34 (t, 2H, H-6'), 4.43 (dd, 1H, H-2', $J_{2',1'}=J_{2',3'}=5.37$ Hz), 4.73 (d, 1H, H-3', $J_{2',3'}=5.37$ Hz), 5.50 (m, 1H, H-1'), 6.08 (dd, 1H, H-5', J=1.5, 3.5 Hz), 8.08 (s, 1H, H-2), 8.19 (s, 1H, H-8).

TLC; Rf=0.28 (Merck, Art 5715 plate developing solvent; chloroform-methanol (5:1).

EXAMPLE 2

Production of 6'-deoxy-6'-chloroneplanocin A:
Triphenylphosphine (341 mg) (1.3 m mol) and carbon tetrachloride (145 μl) (1.5 m mol) were added to neplanocin A (263 mg) (1 m mol) suspended in dimethylformamide (6 ml) and the mixture was stirred at room temperature for 30 mins. The same amounts of triphenylphosphine and carbon tetrachloride as above respectively were added thereto and stirred for two hours. Methanol (5 ml) was added to the reaction mixture, which was stirred for 30 mins. and the solvent was distilled off in vacuo. Chloroform was added to the residue and the insolubles were collected by filtration. The insoluble material was dissolved in a small amount of methanol. The solution mixed with a small amount of silica gel (Merck, Art 9385) was packed in a column, then subjected to column chromatography with elution with chloroform-methanol (30:1), chloroform-methanol (20:1) and chloroform-methanol (15:1), in this order. The fraction eluted with chloroform-methanol (15:1) was dried in vacuo to obtain the product (234 mg) (yield: 83%).

The compound thus obtained has identical physicochemical properties as 6'-deoxy-6'-chloroneplanocin A in Example 1.

EXAMPLE 3

Production of 6'-deoxy-6'-bromoneplanocin A:
In Example 2 carbon tetrachloride was replaced by carbon tetrabromide to obtain the product.
Yield: 216 mg (yield: 66%).
MS (FAB); m/e 306, 328 (MH+).
$^1$H-NMR (400 MHz, DMSO-d6) δ; 4.22 (d, 1H, H-6' b), 4.30 (d, 1H, H-6' a, $J_{6'ab'}=1$ 1 Hz), 4.37 (m, 1H, H-2'), 4.57 (dd, 1H, H-3', $J_{2',3'}=5.37$ Hz), 5.19 (d, 1H, OH), 5.28 (d, 1H, OH), 5.37 (dd, 1H, H-1', $J_{1',2'}=J_{1',5'}=2.44$ Hz), 6.04 (bs, 1H, H-5'), 7.23 (bs, 2H, NH2), 8.08 (bs, 1H, H-2), 8.15 (bs, 1H, H-8).
TLC; Rf=0.32 (merck, Art 5715 plate developing solvent; chloroform-methanol (5:1).

EXAMPLE 4

Production of 6'-deoxy-6'-fluoroneplanocin A:
2',3',-0-isopropylidene-neplanocin A (363 mg) (1.2 m mol) was suspended in dichlormethane (24 ml), the atmosphere inside the reaction vessel consisting of argon gas. Diethylaminosulfurtrifluoride (375 μl) (2 molar equivalent) was poured therein and the mixture was stirred at 0° C. for one hour. The reaction mixture was adjusted to room temperature, and 0.75N aqueous sodium bicarbonate solution (12 ml) was added. The mixture was stirred for 3 mins. and chloroform (60 ml) was added thereto. Insoluble material was removed by filtration and the solution was washed with chloroform (30 ml). The filtrate was separated and the chloroform layer was filtered with Watman 1 ps filter paper, then dried in vacuo. The residue, dissolved in a small amount of chloroform, was charged on a column (4×15 cm) of silica gel (Wako Pure Chem. Co., C-200), then eluted with chloroform and chloroform-methanol (20:1). The fraction eluted with chloroform-methanol (20:1) was dried in vacuo to obtain 6'-deoxy-6'-fluoro-2',3'-O-isopropylidene neplanocin A, a white powder, 123 mg. Yield: 34%.
MS (FAB); m/e 306 (MH+).

¹H-NMR (400 MHz, CDCl₃) δ; 1.50, 1.37 (each s, each 3H, isop-CH₃×2), 4.78 (d, 1H, H-2'), 5.17 (ddd, 2H, H-6', J₆',F=46.9 Hz), 5.44 (d, 1H, H-3', J₂',₃'=5.4 Hz), 5.61 (m, 1H, H-1'), 5.62 (bs, 2H, NH₂) 5.89 (m, 1H, H-5'), 7.69 (s, 1H, H-2), 8.34 (s, 1H, H-8).

TLC; Rf=0.72 (Merck, Art 5715 plate developing solvent; chloroform-methanol (5:1).

The above product (100 mg) (0.33 m mol) dissolved in 50% formic acid (10 ml) was stirred at room temperature for 20 hours. The reaction solvent was removed in vacuo and water was added to the residue, which was then dried in vacuo. Tetrahydrofuran was added to the residue and the thus-formed crystals were filtered to obtain the compound (31 mg). The filtered solution was further concentrated in vacuo. The residue was purified by preparative chromatography using a silica gel plate (Merck, Art 5717) with a developer: chloroform-methanol (5:1), and elution: chloroform-methanol (2:1), to obtain further such compound, 38 mg.

Total yield: 69 mg (yield: 79.4%).

MS (FAB); m/e 266 (MH+).

¹H-NMR (DMSO-d6.D₂O, 400 MHz) δ; 4.38 (dd, 1H, H-2', J=5.9, 5.4 Hz) 4.51 (d 1H, H-3', J=5.4 Hz) 5.06 (dd, 1H H-6' b, J=13.2, 46.9 Hz), 5.13 (ddd, 1H, H-6a, J=2.0, 13.2, 46.9 Hz), 5.40 (m, 1H, H-1'), 5.96 (dd, 1H, H-5', J=2.9, 1.5 Hz), 8.12, 8.11 (each s, each 1H, H-2, H-8).

¹³C-NMR (DMSO-d6, 100 MHz) δ; 64.18 (C-1'), 71.48 (c-3'), 76.11 (C-2'), 79.83 (C-6', J₆',F=161.7 Hz), 119.11 (C-5), 127.76 (C-5', J₅',F=7.6 Hz), 139.83 (C-8), 143.87 (C-4', J₄',F=15.2 Hz), 149.61 (C-4), 152.34 (C-2), 155.88 (C-6).

TLC; Rf=0.24 (Merck, Art 5715 plate developing solvent; chloroform-methanol (5:1).

EXAMPLE 5

Production of 6'-deoxy-6'-iodoneplanocin A:

6'-deoxy-6'-chloroneplanocin A (28 mg) (0.1 m mol) and LiI (67 mg) (5 molar equivalent) were refluxed in acetonitrile (3 ml) for 15 mins. The reaction mixture was ice cooled and the solvent was removed in vacuo. The residue, dissolved in a small amount of methanol, was purified by preparative chromatography using a silica gel plate (Merck, Art 5717) with developer: chloroform-methanol (5:1) and an elution: chloroform-methanol (2:1) to obtain the product (12 mg). (Yield: 32%).

¹H-NMR (CD₃OD, 90 MHz) δ; 4.36 (dd, 1H, H-2', J=4.7 Hz, 5.6 Hz), 4.84 (d, 1H, H-3'), 5.43 (m, 1H, H-1'), 6.10 (m, 1H, H-5'), 7.99 (s, 1H, H-2), 8.18 (s, 1H, H-8).

TLC; Rf=0.38 (Merck, Art 5715 plate developing solvent; chloroform-methanol (5:1).

What is claimed is:

1. A compound of the formula

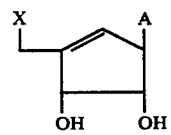

wherein A is adenine-9-yl and X is halogen, or a pharmaceutically acceptable salt thereof, said compound or salt being isolated from other compounds present during its production.

2. A pharmaceutical composition for producing a cytotoxic effect, comprising:
a compound of the formula

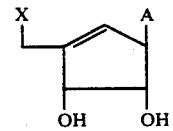

wherein A is adenine-9-yl and X is halogen, or a pharmaceutically acceptable salt of said compound; in combination with a pharmaceutical diluent; said compound or salt being present in an amount effective to produce a cytotoxic effect.

* * * * *